(12) United States Patent
Mellejor et al.

(10) Patent No.: US 9,884,173 B2
(45) Date of Patent: *Feb. 6, 2018

(54) MEDICAMENT APPLICATOR

(71) Applicant: Kashiv Pharma, LLC, Bridgewater, NJ (US)

(72) Inventors: Jamelo J. Mellejor, Bridgewater, NJ (US); Sanjeev K. Gupta, Bridgewater, NJ (US); Dipen Desai, Whippany, NJ (US)

(73) Assignee: Kashiv Pharma, LLC, Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/344,803

(22) Filed: Nov. 7, 2016

(65) Prior Publication Data
US 2017/0050007 A1    Feb. 23, 2017

Related U.S. Application Data

(63) Continuation of application No. 13/921,429, filed on Jun. 19, 2013, now Pat. No. 9,517,328.

(51) Int. Cl.
*A61M 31/00*    (2006.01)
*A61M 5/315*    (2006.01)
(Continued)

(52) U.S. Cl.
CPC ........ *A61M 31/007* (2013.01); *A61M 3/0262* (2013.01); *A61M 5/178* (2013.01); *A61M 5/315* (2013.01); *A61M 5/31501* (2013.01); *A61M 37/0069* (2013.01); *A61M 2005/005* (2013.01); *A61M 2210/14* (2013.01)

(58) Field of Classification Search
CPC ............ A61M 3/0071; A61M 5/31501; A61M 5/315; A61M 5/178; A61M 3/0262; A61M 31/007; A61M 37/0069; A61M 2005/005; A61M 2210/14
USPC ..... 604/11–18, 110, 187, 218, 220, 219, 59, 604/515
See application file for complete search history.

(56) References Cited

U.S. PATENT DOCUMENTS 2,754,822 A    7/1956    Emelock
3,635,218 A    1/1972    Ericson
(Continued)

FOREIGN PATENT DOCUMENTS

AU    570785 B2    3/1988
DE    8409756 U1    8/1984
(Continued)

OTHER PUBLICATIONS

International Search Report and Written Opinion for Application No. PCT/US2014/042318 dated Oct. 10, 2014.

*Primary Examiner* — Manuel Mendez
(74) *Attorney, Agent, or Firm* — Lerner, David, Littenberg, Krumholz & Mentlik, LLP

(57) ABSTRACT

Apparatus and methods for inserting a medicament into a body cavity are described. The apparatus comprises an elongate tube with a plunger rod therein. The plunger rod has at least one projection which cooperatively interacts or engages with at least one discontinuity on the inside of the elongate tube so that proximal movement of the plunger rod with respect to the elongate tube expels the medicament into the body cavity.

26 Claims, 8 Drawing Sheets

(51) Int. Cl.
*A61M 37/00* (2006.01)
*A61M 5/178* (2006.01)
*A61M 3/02* (2006.01)
*A61M 5/00* (2006.01)

(56) References Cited

U.S. PATENT DOCUMENTS

| | | | |
|---|---|---|---|
| 3,766,921 A * | 10/1973 | Dulle | A61F 13/2051 604/12 |
| 3,780,735 A | 12/1973 | Crouter et al. | |
| 4,341,211 A | 7/1982 | Kline | |
| 4,361,150 A | 11/1982 | Voss | |
| 4,421,504 A * | 12/1983 | Kline | A61M 31/007 604/12 |
| 4,496,341 A | 1/1985 | Brucks | |
| 4,826,483 A * | 5/1989 | Molnar, IV | A61M 5/5013 604/110 |
| 4,911,687 A * | 3/1990 | Stewart | A61F 13/34 604/11 |
| 4,978,339 A | 12/1990 | Labouze et al. | |
| 4,990,136 A | 2/1991 | Gena | |
| 5,084,017 A * | 1/1992 | Maffetone | A61M 5/5066 604/110 |
| 5,213,566 A | 5/1993 | Weissenburger | |
| 5,250,030 A * | 10/1993 | Corsich | A61M 5/5013 604/110 |
| 5,263,934 A | 11/1993 | Haak | |
| 5,330,427 A | 7/1994 | Weissenburger | |
| 5,352,208 A | 10/1994 | Robinson | |
| 5,380,295 A * | 1/1995 | Vacca | A61M 5/315 604/187 |
| 5,395,308 A | 3/1995 | Fox et al. | |
| 5,697,918 A * | 12/1997 | Fischer | A61O 5/062 433/90 |
| 5,738,646 A | 4/1998 | Fox et al. | |
| 5,788,664 A | 8/1998 | Scalise | |
| 5,860,946 A | 1/1999 | Hofstatter | |
| 7,104,968 B2 | 9/2006 | Swick | |
| 7,217,252 B2 | 5/2007 | Swick | |
| 7,591,808 B2 | 9/2009 | DiPiano et al. | |
| 7,666,160 B2 | 2/2010 | Rajala et al. | |
| 8,057,433 B2 | 11/2011 | Cuca et al. | |
| 8,338,396 B2 | 12/2012 | Bell et al. | |
| 9,517,328 B2 * | 12/2016 | Mellejor | A61M 5/31501 |
| 2004/0260252 A1 | 12/2004 | DiPiano et al. | |
| 2005/0010160 A1 * | 1/2005 | Loomis | A61M 31/007 604/11 |
| 2007/0225655 A1 | 9/2007 | Osinga | |
| 2008/0097388 A1 | 4/2008 | Cuca et al. | |
| 2008/0243046 A1 | 10/2008 | Cettina et al. | |
| 2010/0010471 A1 * | 1/2010 | Ladd | A61M 31/007 604/514 |
| 2011/0009829 A1 | 1/2011 | Kosinski et al. | |

FOREIGN PATENT DOCUMENTS

| | | |
|---|---|---|
| EP | 1371386 A2 | 12/2003 |
| FR | 2561928 A3 | 10/1985 |
| WO | 8400495 A1 | 2/1984 |
| WO | 0066213 A1 | 11/2000 |
| WO | 2006121754 A2 | 11/2006 |

* cited by examiner

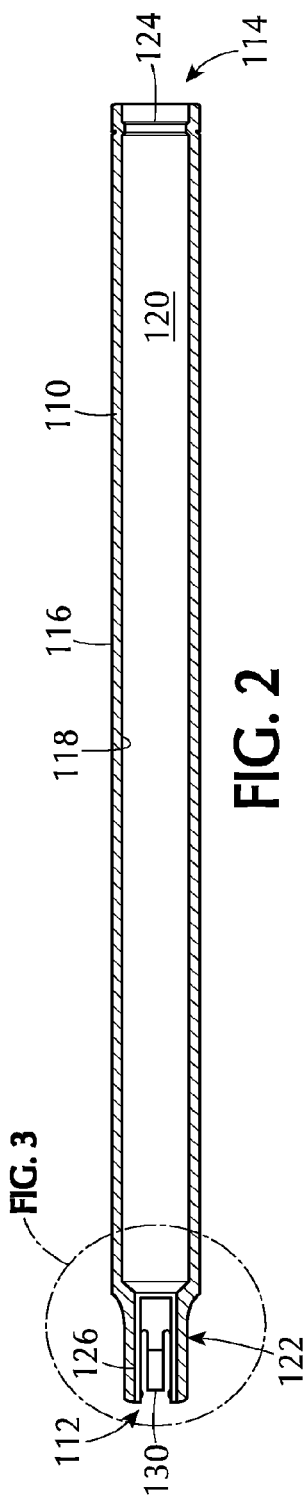
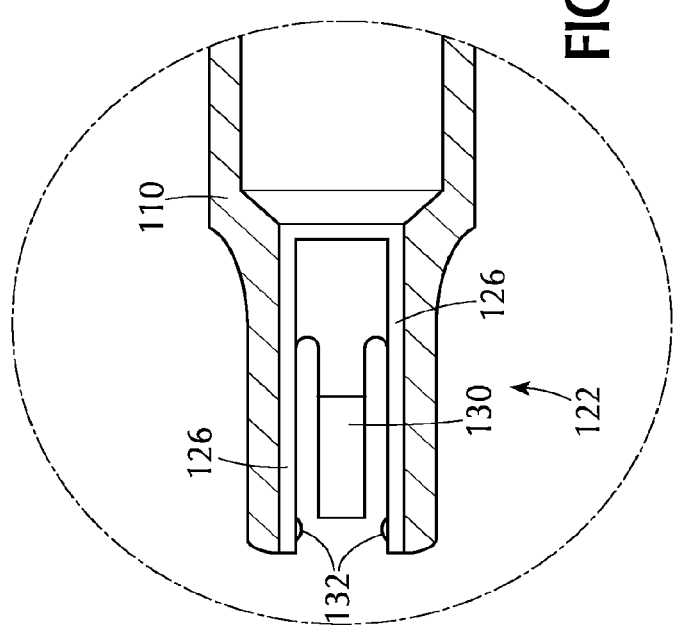

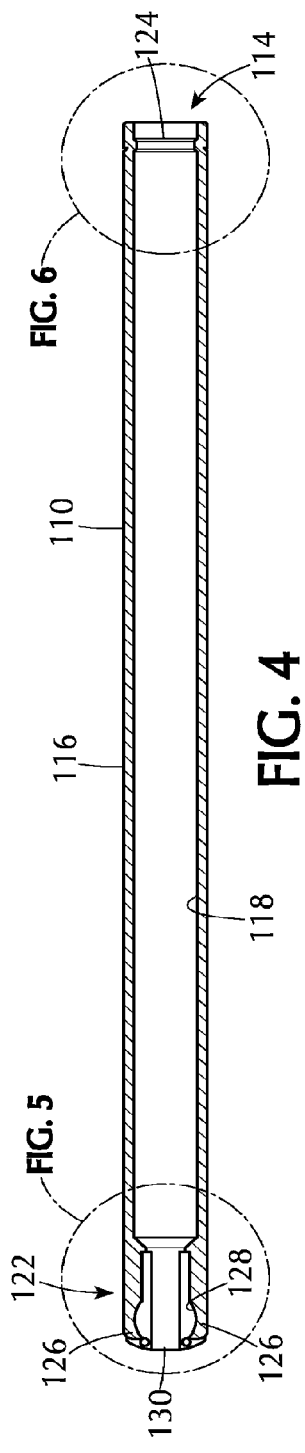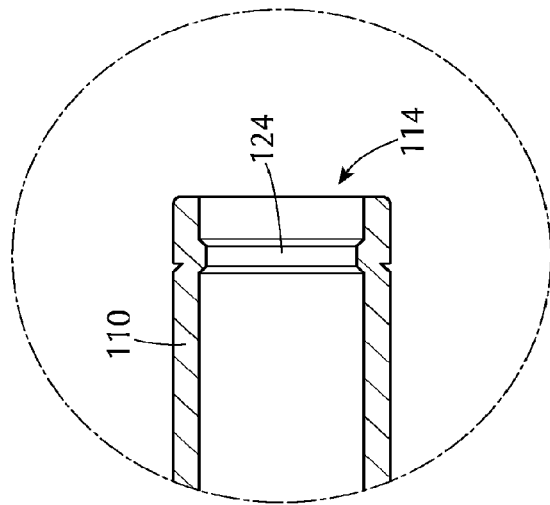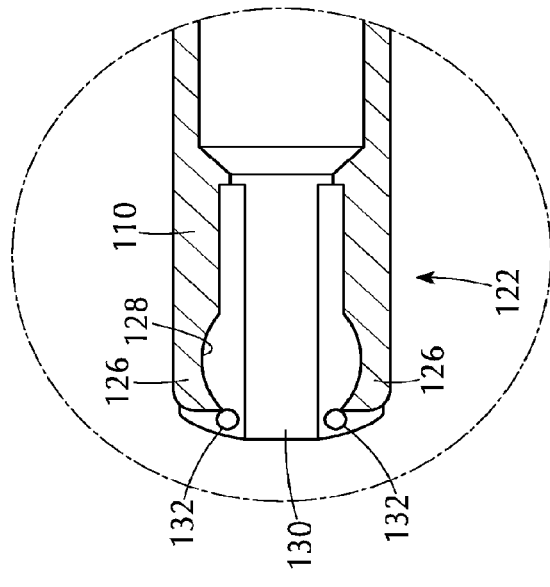

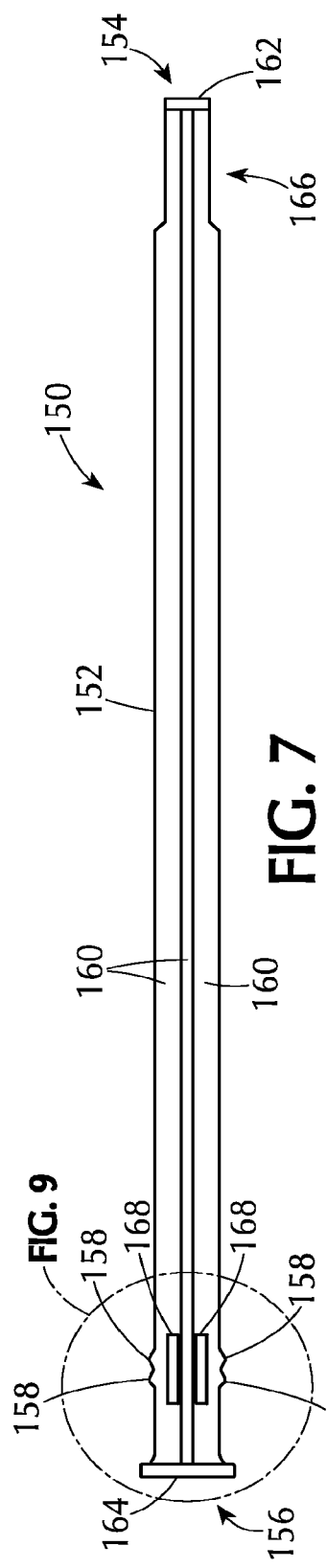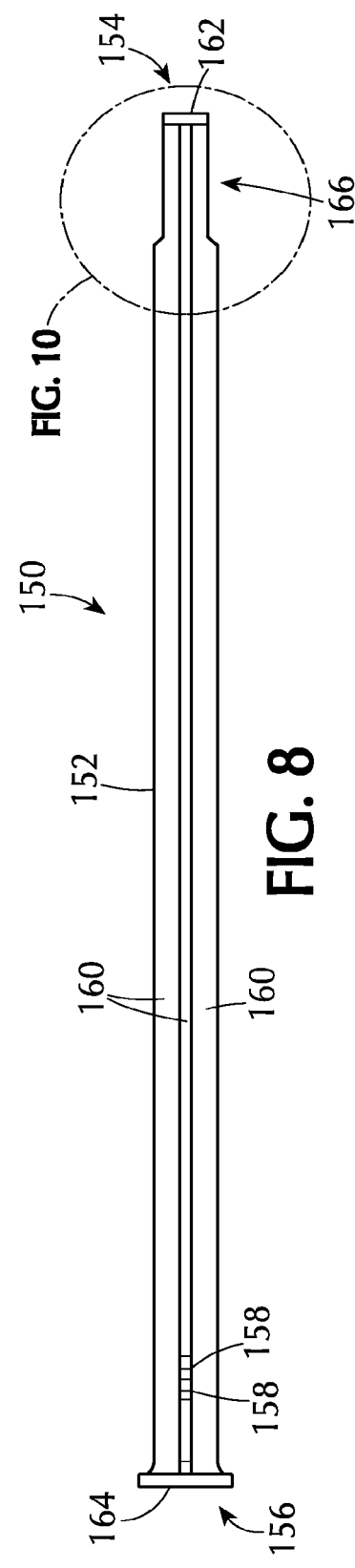

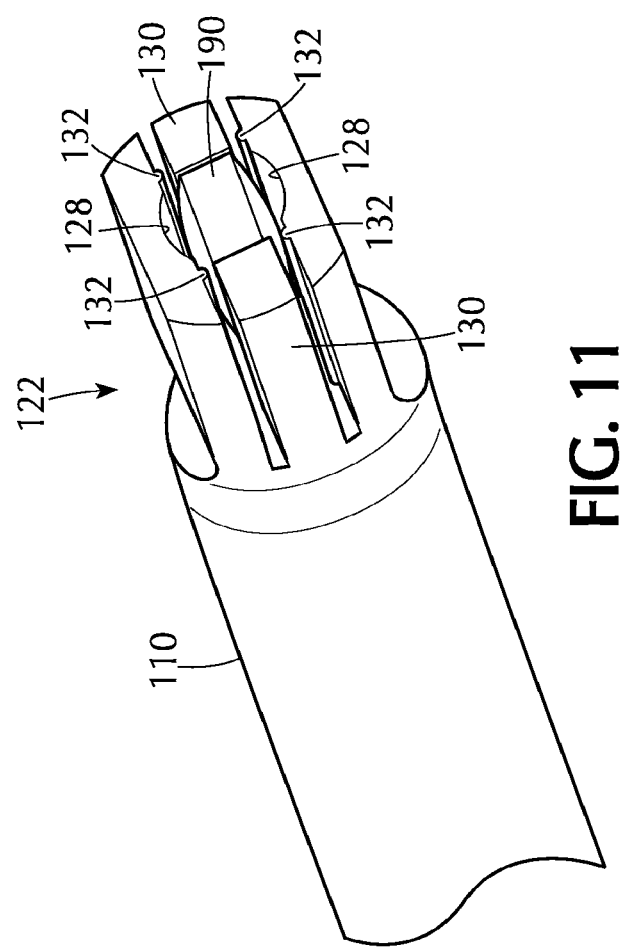

MEDICAMENT APPLICATOR

BACKGROUND OF THE INVENTION

Aspects of the present disclosure generally relate to an apparatus and a method for introducing a medicament into a body cavity. Specific embodiments of the disclosure are directed to apparatus and methods for administering a medicament vaginally.

Instruments for inserting a suppository commonly hold the suppository at a first end of a tubular body with a plunger rod accessible from a second end of the tubular body to forcefully expel the suppository. Before use, the typical suppository insertion tool has a loosely-positioned plunger rod within the tubular body. Support structures hold the plunger rod in place to prevent it from becoming dislodged from the tubular body to avoid contamination of the plunger rod. Contamination of the plunger rod with foreign matter and/or microorganisms is undesirable as these contaminants can be transferred to the user.

Some suppository insertion tools include a flange/shoulder combination to hold the plunger rod in place. These flange/shoulder combinations are positioned immediately adjacent the suppository being used. This placement is useful to support the suppository prior to use. However, pressure on the other end of the plunger rod, for example, when operating the tool, can cause the plunger rod to deform and bow along its length. If the plunger rod becomes bowed, the end of the plunger rod adjacent the suppository becomes skewed and can damage the suppository during insertion and/or adversely affect a desired straight trajectory of the expelled suppository.

There is a continuing need in the art for reliable and cost effective medicament dose insertion devices. The devices need to be simple in design, to promote both ease of manufacturing and patient compliance. In addition, many existing commercially available devices do not reproducibly deliver medicaments, as can be indicated by measuring the distances traveled by expelled dosage forms when the devices are actuated.

SUMMARY OF THE INVENTION

An aspect of the present disclosure provides an assembly for introducing a medicament into a body cavity, the assembly comprising: an elongate tube having a proximal end, a distal end, an outer surface, an inner surface and an opening extending from the distal end to the proximal end, the proximal end adapted to support a medicament, the elongate tube comprising at least one radial discontinuity adjacent the distal end and extending inwardly from the inner surface of the tube; and a plunger rod having an elongate body with a distal end and a proximal end, the plunger rod adapted to be slidably engaged within the tube, the plunger rod comprising at least two axially spaced projections adjacent the distal end of the elongate body that cooperatively engages with the at least one radial discontinuity.

In embodiments, the proximal end of the elongate tube contains a medicament. In certain embodiments, the medicament is a tablet.

BRIEF DESCRIPTION OF THE DRAWINGS

FIG. 2 shows a cross-sectional view of an elongate tube in accordance with one or more embodiments of the disclosure;

FIG. 3 shows an expanded view of a portion of the elongate tube of FIG. 2;

FIG. 4 shows a cross-sectional view of an elongate tube in accordance with one or more embodiments of the disclosure;

FIG. 5 shows an expanded view of a portion of the elongate tube of FIG. 4;

FIG. 6 shows an expanded view of a portion of the elongate tube of FIG. 4;

FIG. 7 shows a cross-sectional view of a plunger rod in accordance with one or more embodiments of the disclosure;

FIG. 8 shows a cross-sectional view of a plunger rod in accordance with one or more embodiments of the disclosure;

FIG. 11 shows a partial perspective view of a medicament insertion tool in accordance with one or more embodiments of the disclosure;

DETAILED DESCRIPTION

Medicaments that can be delivered using an apparatus of the present disclosure can be in the forms of inserts (i.e., tablets or suppositories), capsules, creams, gels, etc. Drug substances that can be incorporated into the medicaments include those suitable for either human or veterinary therapy. In embodiments, the medicaments are intended for oral administration when human or veterinary patients will not readily swallow a dosage form. In other embodiments, medicaments are intended for administration into a body cavity or onto the eye, where a drug will have a local effect or be absorbed through mucosa.

For purposes of illustration, an applicator device particularly suited for administering a solid dosage form intravaginally will be described below. Those skilled in the art will be aware of modifications that can be made for administering medicaments of various other types into other body cavities. By selecting an appropriate body length, embodiments of the device described below can be used for intrauterine medicament administration.

Figure 1:
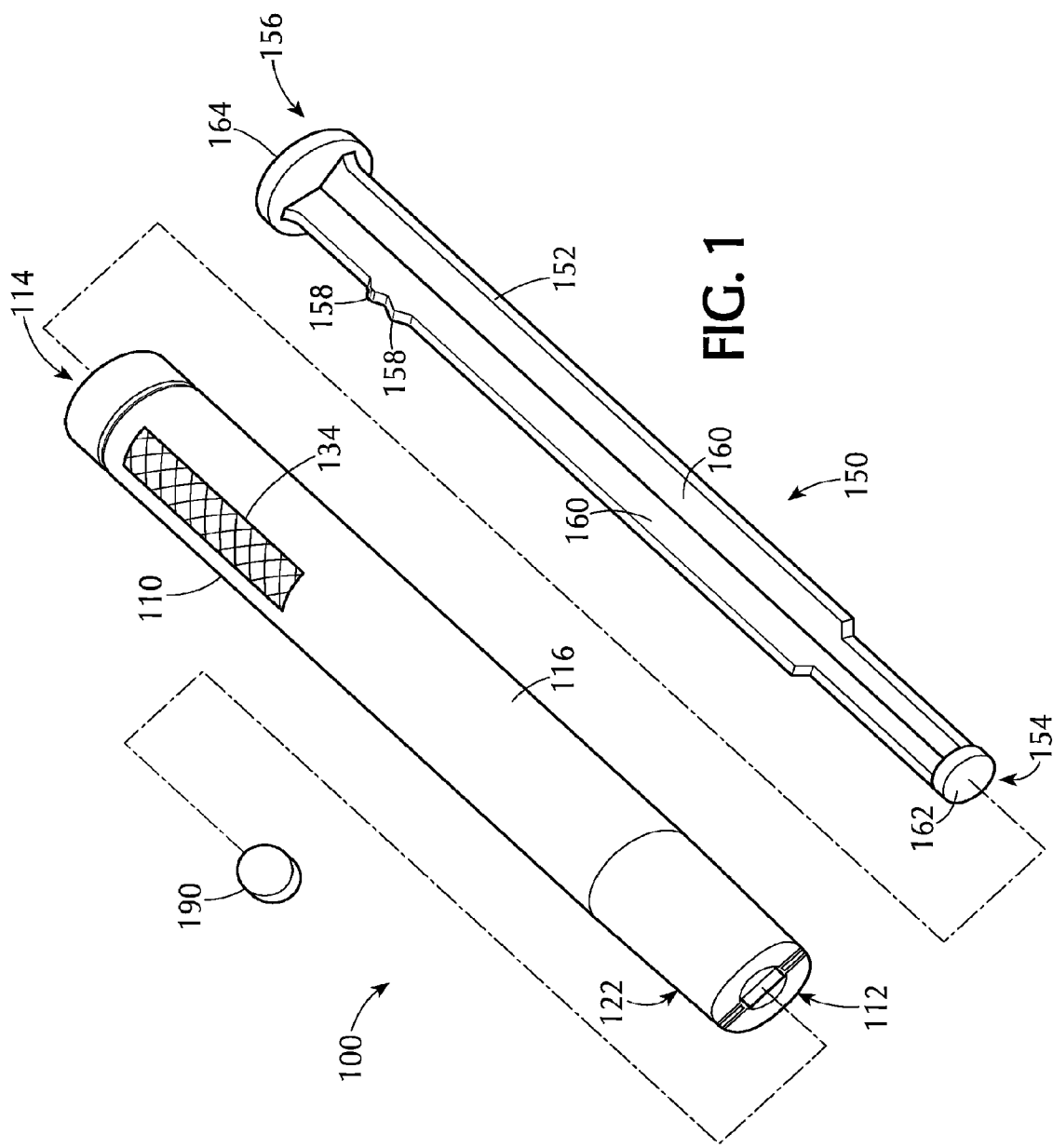
FIG. 1 shows an exploded perspective view of a medicament insertion tool in accordance with one or more embodiments of the disclosure.
Figure 10:
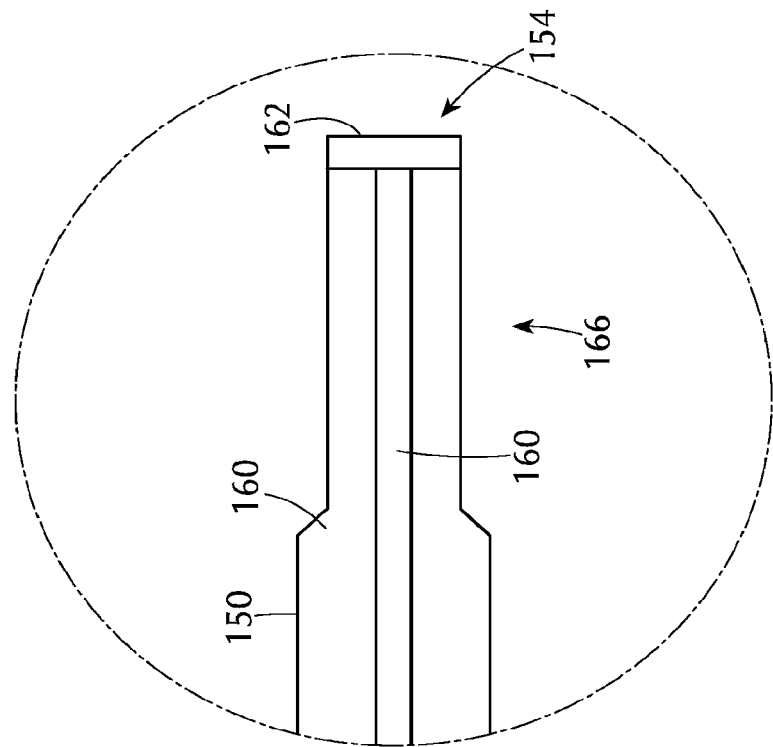
FIG. 10 shows an expanded view of a portion of the plunger rod of FIG. 8.
Figure 9:
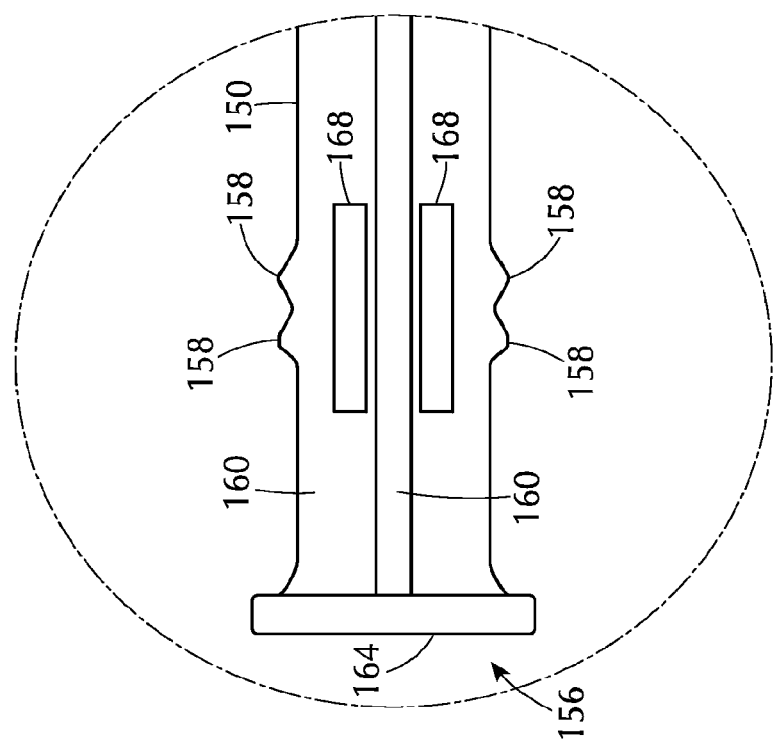
FIG. 9 shows an expanded view of a portion of the plunger rod of FIG. 7.

Referring to FIG. 1, one or more embodiments are directed to assemblies 100 for inserting a solid dosage form, such as tablet 190, into a body cavity. The body cavity can be any suitable body cavity depending on the medication to be delivered. In some embodiments, the body cavity is one or more of a mouth, vagina, nostril, ear, or anus. The assemblies 100 comprise an elongate tube 110, also referred to as a barrel, and a plunger rod 150. Some embodiments of the assembly 100 further comprise a tablet 190.

FIGS. 1 to 6 show embodiments of elongate tubes 110 in accordance with one or more embodiments. The elongate tube 110 has a proximal end 112, a distal end 114, an outer surface 116 and an inner surface 118. An opening 120 extends from the distal end 114 to the proximal end 112 and forms a cavity within the elongate tube 110. The cavity holds and guides the plunger rod 150 as it moves to expel the medicament.

The shape of the elongate tube 110, in cross-section, can be any suitable shape including, but not limited to, circular, elliptical, square, triangular, pentagonal, hexagonal or octagonal. The elongate tube 110 shown in the figures has a round cross-section so that the majority of the elongate tube appears to be cylindrical. The shape of the cavity can be the same or different from the outer shape. For example, the outer surface of the elongate tube 110 may have a hexagonal cross-section, while the cavity on the inner surface is circular.

The proximal end 112 of the elongate tube 110 includes a support section 122. The support section 122 supports a tablet 190, capsule, suppository or other suitable medication dosage form. In some embodiments, the support section 122 or proximal end 112 supports a medicament for delivery to a body cavity. Although the term "tablet" is sometimes used throughout this specification to describe the medicament, it will be understood by those skilled in the art that the dosage form is not limited to tablets.

The support section 122 at the proximal end 112 of the elongate tube 110 may include one or more components to support the medicament. In some embodiments, as shown in FIGS. 3-5, the support section 122, or proximal end 112 of the elongate tube 110, includes at least two tongues 126 that can support the medicament. The tongues 126 can be shaped to conform to the shape of the medicament so that there is greater surface area contact between the tongue and the medicament. For example, in some embodiments the tongues 126 comprise concave walls 128 which engage a convex surface of the medicament. The at least two tongues 126 help prevent the medicament from being prematurely expelled from the proximal end 112 of the elongate tube 110.

In some embodiments, the proximal end 112 of the elongate tube 110 includes at least two lips 130. One more of the lips 130 and tongues 126 can be present. In some embodiments, both lips 130 and tongues 126 are present. The at least two lips 130 help prevent lateral movement of the medicament. As a result, the lips 130 help hold the medicament in place until the user is ready to expel the medicament. The at least two lips 130 of some embodiments are biased inwardly from the outer surface of the elongate tube 110. The lips 130 can also be shaped to conform to the medicament in similar fashion as the tongues 126. This may allow the lips 130 to be more effective at retaining the medicament so that there is a decreased potential for premature expulsion of the medicament.

Some embodiments of the elongate tube 110 include at least one tooth 132 at the support section 122. The at least one tooth 132 can be seen in FIGS. 3 and 5 and are positioned on the tongues 126. The at least one tooth 132 extends inwardly from the tongues 126 and can serve to prevent the medicament from being prematurely expelled by providing an additional barrier that must be overcome during expulsion. The number of teeth 132 can vary depending on the specific shape and size of the medicament and the support section 122. In some embodiments, each tongue 126 has at least one tooth 132. In one or more embodiments, each tongue 126, as shown in the Figures, has at least two teeth 132.

The specific medication in the tablet, capsule, etc., is dependent only on the desired treatment. In one or more embodiments, a tablet comprises an estrogen, such as estradiol, and, optionally, may also include any suitable binders, fillers and excipients. In some embodiments, a tablet comprises an estrogen in an amount up to about 50 mcg (micrograms). In one or more embodiments, a tablet comprises an estrogen in an amount in the range of about 5 mcg to about 40 mcg. In some embodiments, a tablet comprises an estrogen in an amount in the range of about 10 mcg to about 25 mcg.

The elongate tube 110 includes at least one radial discontinuity 124 about the inner surface 118. The at least one radial discontinuity 124 of some embodiments is spaced a distance from the distal end 114 of the elongate tube 110 as shown in the Figures. However, it will be understood by those skilled in the art that the radial discontinuity 124 can be positioned immediately adjacent the distal end 114. In one or more embodiments, the radial discontinuity 124 is positioned at a distance of up to about 50% of the overall length of the elongate tube 110 from the distal end 114, so that the at least one radial discontinuity is positioned closer to the distal end 114 than to the proximal end 112 of the elongate tube 110. In some embodiments, the at least one radial discontinuity is at least about 0.05 inches from the distal end, or in the range of 0.03 to 0.09 inches from the distal end. Without being bound by any particular theory of operation, it is believed that this placement of the radial discontinuity prevents or minimizes deformation and bowing of the plunger rod 150 during use.

As used in this specification and the appended claims, the term "discontinuity" means any intentional irregularity in the smoothness of the inner surface 118 of the elongate tube 110. The radial discontinuity 124 can be one or more of a projection and a recess. In the embodiment shown in the Figures, the radial discontinuity 124 is a projection extending inwardly from the inner surface 118 of the elongate tube 110. As will be discussed further below, the shape of the discontinuity is such that the discontinuity can cooperatively interact or engage with at least one projection on the plunger rod. In some embodiments, the discontinuity is a recess and the plunger rod includes at least one projection that cooperatively interacts or engages with the recess.

The embodiment of FIG. 1 includes a roughened area or corrugations 134 on the outer surface 116 of the elongate tube 110. The corrugations 134 can be any suitable pattern or configuration and provide a textured area for a user to grip the assembly 100. The corrugations 134 of some embodiments help to prevent slippage of the elongate tube between the user's fingers. The corrugations 134 can be, for example, cross-hatched or bumps and be formed into any shape. For example, the corrugations 134 can include a logo, product or company name embossed therein, or the corrugations 134 can form a logo, product or company name.

The dimensions of the elongate tube 110 can vary depending on the desired use of the insertion tool. In some embodiments, the elongate tube has a length in the range of about 4 inches to about 6 inches, or in the range of about 4.5 inches to about 5.5 inches, or in the range of about 4.8 inches to about 5 inches. In one or more embodiments, the elongate tube has a length of about 4.906 inches ±1%. The diameter of the elongate tube can also vary depending on, for example, the medicament to be dispensed from the elongate tube. In some embodiments, the elongate tube has an outer diameter in the range of about 0.1 inches to about 0.8 inches, or in the range of about 0.2 inches to about 0.6 inches, or in the range of about 0.3 inches to about 0.4 inches. In one or more embodiments, the elongate tube has an outer diameter of about 0.314 inches ±0.5%.

Referring to FIGS. 7 to 10, the assembly 100 includes a plunger rod 150 which can be used to expel the medicament from the support section 122. The plunger rod 150 has an elongate body 152 with a proximal end 154 and a distal end 156 and can slidably engage the elongate tube 110 within the cavity. The plunger rod comprises at least one projection adjacent the distal end 156 of the elongate body 152. The at least one projection 158 is sized and shaped to cooperatively interact with, or engage, the at least one radial discontinuity 124 on the inner surface 118 of the elongate tube 110.

In some embodiments, there are at least two axially spaced projections 158 on the elongate body 152. The at least two axially spaced projections 158 can cooperatively interact with, or engage, the at least one radial discontinuity 124. The embodiments shown in the Figures include two axially spaced projections 158. Including at least two projections 158 can provide additional control over the positioning of the plunger rod 150 within the elongate tube 110 as described further below.

The plunger rod 150 can be solid or hollow and has a cross-sectional shape that will allow it to slide within the elongate tube 110. For example, if the elongate tube has a round, triangular, or square cross-sectional shape, the plunger rod can have a similar shape. However, it is not always necessary for the shapes to be similar.

As shown in the Figures, the elongate body 152 of the plunger rod 150 of an embodiment comprises at least two intersecting beams 160. The intersecting beams 160 extend from the distal end 156 to the proximal end 154 of the plunger rod 150. In one or more embodiments, there are two intersecting beams 160 such that elongate body 152 has a cruciform-shaped cross section comprising four rays. In some embodiments, the plunger rod 150 comprises three intersecting beams 160, or more, such that there are six rays (or two times the number of beams). The number of rays including projections 158 can vary depending on, for example, the size of the assembly, plunger rod and medicament to be delivered. In some embodiments, two of the four rays contain at least one projection 158. In one or more embodiments, two of four rays contain two axially spaced projections 158 as illustrated in the Figures.

In some embodiments, the proximal end 154 of the plunger rod 150 is undivided. This means that the proximal end 154 of the plunger rod 150 is a solid material and does not contain specific definable rays. In these embodiments, the intersecting beams 160 extend from the distal end 156 toward the proximal end 154 of the plunger rod 150 and either taper or abruptly transition to the undivided portion.

The proximal end 154 of the plunger rod 150 can have any shape suitable for contacting and expelling the medicament. In some embodiments, the proximal end 154 of the plunger rod 150 is blunt. This can be seen in the Figures as a proximal cap 162 on the proximal end 154 of the plunger rod 150. The proximal cap 162 can be blunt (or flat ended) or have a shape conforming to the portion of the medicament that the proximal cap 162 will contact. In other embodiments, the proximal end 154 has a rounded surface. Various embodiments avoid providing any sharp edges that might come into contact with patient epithelial tissues. In certain embodiments, the length of plunger rod 150 is such that the rod will remain substantially completely within elongate body 152 after a medicament has been expelled, thereby avoiding contact between the plunger rod and epithelial tissues.

The pushing region 166 of the plunger rod 150 can be the same size (e.g., radially) or a different size than the remainder of the plunger rod 150. For example, the pushing region 166 of the plunger rod shown in the Figures is smaller than the remainder of the plunger rod 150. In some embodiments where the pushing region 166 is smaller than the rest of the plunger rod, the pushing region and the proximal cap 162 are more easily able to fit into the support section 122 to expel the medicament. The support section 122 may have components (e.g., fingers, tongues and teeth) which make the support section 122 smaller than the remainder of the elongate tube 110. Therefore, if the pushing region 166 of the plunger rod 150 is smaller in diameter, then the pushing region 166 will more easily fit into the support section 122.

The distal end 156 of the plunger rod 150 may also include a thumbpress 164 which can be smooth or textured. In some embodiments, the thumbpress 164 is textured to prevent slippage of the user's thumb or finger from the thumbpress 164.

The plunger rod 150 may also include one or more openings 168 adjacent the at least one projection 158. The openings 168 can be positioned along the rays containing the projections adjacent the projections. Without being bound by any particular theory of operation, it is believed that the openings allow for some flexing in the plunger rod 150 at the projections 158 so that the projections can move relative to the at least one discontinuity.

Figure 12A:
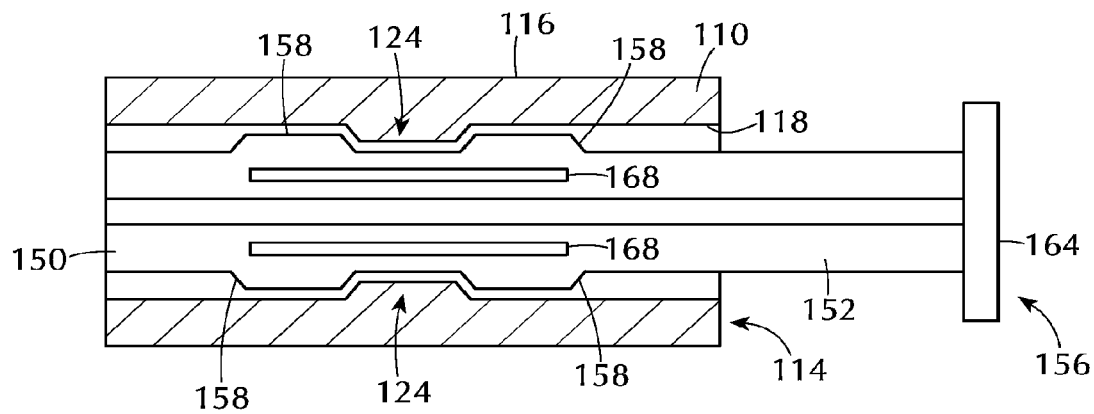
FIG. 12A shows an expanded view of the distal end of a medicament insertion tool in the ready-to-use configuration in accordance with one or more embodiments of the disclosure.

In some embodiments, as shown in FIG. 12A, the at least one radial discontinuity 124 on the elongate tube 110 is cooperatively engaged between the at least two axially spaced projections 158 on the elongate body of the plunger rod 150. Such an arrangement is suitable to substantially prevent spontaneous movement of the plunger rod 150 distally or proximally with respect to the elongate tube 110. As used in this specification and the appended claims, the term "substantially prevent spontaneous movement" means that the plunger rod does not move distally or proximally with respect to the elongate tube 110 to the extent that one or more of the projections moves past the at least one discontinuity or that the medicament is spontaneously expelled from the assembly. This means that minor movement of the plunger rod either distally or proximally with respect to the elongate tube is possible, but such movement is inconsequential to the operation of the assembly.

The physical dimensions of the plunger rod 150 can vary depending on the desired use of the suppository insertion tool. The dimensions of the plunger rod allow the plunger rod to cooperatively interact with the elongate tube. In some embodiments, the plunger rod has a length in the range of about 4 inches to about 6 inches, or in the range of about 4.5 inches to about 5.5 inches, or in the range of about 4.8 inches to about 5 inches. In one or more embodiments, the plunger rod has a length of about 4.960 inches ±1%. The diameter of the plunger rod can also vary depending on, for example, the medicament to be dispensed from the elongate tube. In some embodiments, the plunger rod has a diameter near the proximal end in the range of about 0.05 inches to about 0.6 inches, or in the range of about 0.1 inches to about 0.4 inches, or in the range of about 0.14 inches to about 0.15 inches. In one or more embodiments, the elongate tube has an outer diameter of about 0.141 inches ±1%.

The operation of one or more embodiments of the assembly is described with respect to FIGS. 12 and 13. As shown in FIG. 12A, the at least two axially spaced projections 158 on the elongate body 152 of the plunger rod 150 are positioned on opposite sides of the at least one discontinuity 124 on the inner surface 118 of the elongate tube 110. The plunger rod 150 can be placed into this position during manufacturing of the assembly (i.e., before sale of a completed unit) or after manufacture (i.e., by an end user). The position of the plunger rod 150 shown in FIG. 12A substantially prevents proximal or distal movement of the plunger rod. This position may be useful to ensure that the end user has the assembly in a ready-to-use configuration.

Figure 12B:
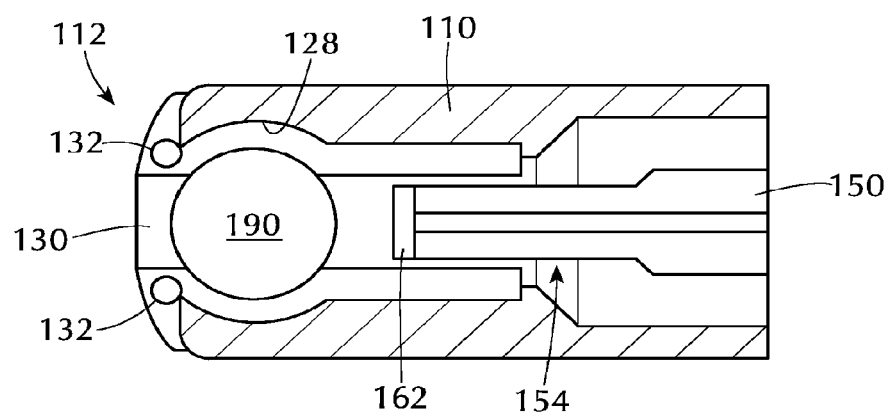
FIG. 12B shows an expanded view of the proximal end of a medicament insertion tool in the ready-to-use configuration in accordance with one or more embodiments of the disclosure.

The at least one projection 158 is shown positioned at a sufficient distance from the distal end 156 of the plunger rod 150 such that the proximal end 154 of the plunger rod 150, and the proximal cap 162, are positioned distally from the tablet 190. Referring to FIG. 12B, the proximal end 154 of the plunger rod 150 is in position to expel the tablet 190 upon proximal movement of the plunger rod 150. However, because of the placement of the projections 158 relative to the at least one discontinuity 124, expulsion cannot occur spontaneously. In the positions shown in FIGS. 12A and 12B, the assembly is loaded with a tablet 190 and ready for use.

Figure 13A:
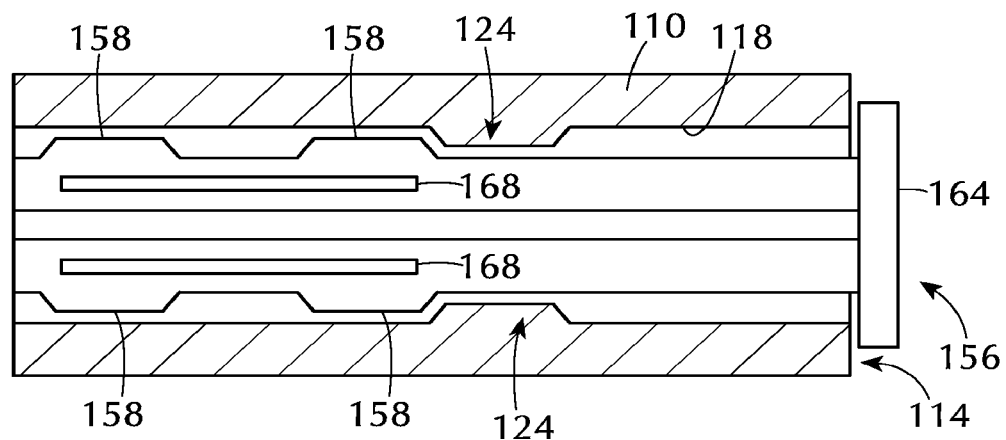
FIG. 13A shows an expanded view of the distal end of a medicament insertion tool after delivery, in accordance with one or more embodiments of the disclosure.
Figure 13B:
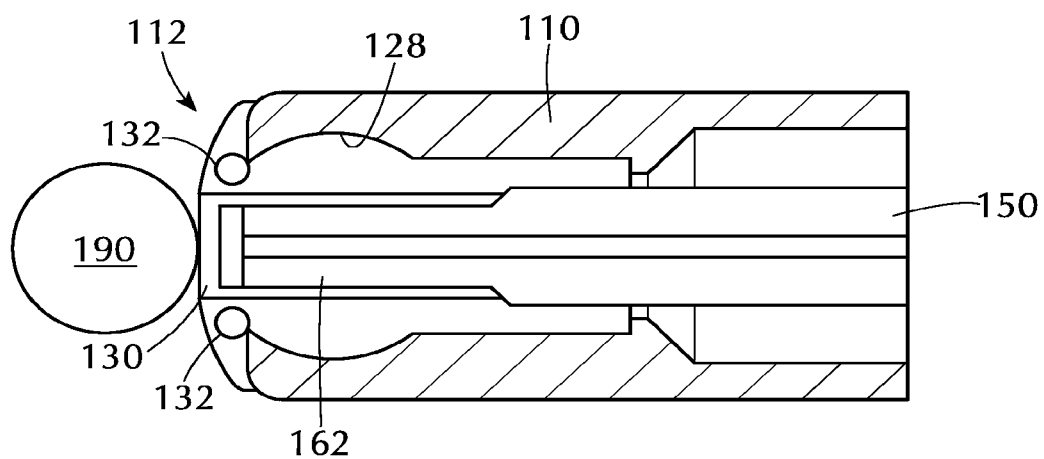
FIG. 13B shows an expanded view of the proximal end of a medicament insertion tool after delivery, in accordance with one or more embodiments of the disclosure.

Referring to FIGS. 13A and 13B, proximal movement of the plunger rod 150 relative to the elongate tube 110 expels the tablet 190. In FIG. 13A, it can be seen that both of the projections 158 on the plunger rod 150 have been moved proximal of the at least one discontinuity 124. Since this cannot occur spontaneously, it will likely be the result of proximally directed force on the plunger rod 150. For example, the user may apply pressure to the thumbpress 164 to expel the tablet 190. In FIG. 13B, the proximal cap 162 of the plunger rod 150 has contacted the tablet 190 and forced it out of the elongate tube 110. If the proximal end 112 of the elongate tube 110 has been positioned in a body cavity, the tablet 190 will be expelled into that cavity.

The projections 158 on the plunger rod 150 may be positioned a distance from the distal end 156 of the plunger rod 150 and the thumbpress 164, so that proximal movement of the plunger rod 150 causes the thumbpress 164 to contact the distal end 114 of the elongate tube 110. The contact of the thumbpress 164 with the elongate tube 110 may serve to stop further proximal movement so that the proximal cap of the plunger rod 150 does not protrude from the proximal end of the elongate tube 110. The distance between the thumbpress 164 and the projections 158 can be tuned to allow or prevent such protrusion.

In alternate embodiments, there are two radial discontinuities 124 on the inner surface 118 of the elongate tube 110. The radial discontinuities 124 are spaced along the length of the elongate tube 110 so that there is a distal discontinuity and a proximal discontinuity. The plunger rod 150 includes a single projection 158 which can be moved from the distal discontinuity to the proximal discontinuity. In the ready-to-use position, the projection 158 is engaged with the distal discontinuity which holds the plunger rod in position to expel the medicament. When force is applied to the thumbpress in the proximal direction, the projection 158 slides from the distal discontinuity to the proximal discontinuity, and the proximal end of the plunger rod expels the medicament.

Both the elongate tube 110 and the plunger rod 150 can be made from any suitable materials. Additionally, each component can be integrally formed or made up of multiple pieces. In some embodiments, each of the elongate tube and the plunger rod are independently made from a material comprising one or more of polypropylene and high-density polyethylene. The apparatus is well-suited for inexpensive component manufacturing from any desired thermoplastic materials, using single- or multiple-cavity molds. In embodiments, the apparatus is intended for delivering a prefilled medicament and will be discarded after use.

Embodiments of the disclosed apparatus can reproducibly expel a 6 mm diameter tablet to distances at least 10 inches from the proximal tip.

Certain modifications can be made to the apparatus for delivering fluid medicaments, such as semi-solid creams, gels, etc., and liquids. For such medicaments, the proximal end of the elongate tube will not have the above-described support section for retaining a solid dosage form but rather will have a substantially uniform internal shape and be capable of being closed, such as with a removable plug, to contain and protect the contained medicament until it is intended to be dispensed. The plunger tip also will have a sealing relationship with the interior surface of the elongate tube. In embodiments, the proximal end can be fitted with a tip that enables delivery of a medicament in desired dimensions, and facilitates application onto a desired portion of the anatomy. The tip can be affixed after removal of the closure, or can be permanently or removably attached during manufacture of the elongate tube or after filling of the medicament into the tube. For fluid medicaments, the contained medicament quantity can be delivered in a single step or can be delivered in portions, at different times and/or to different locations.

Applicator devices, constructed in accordance with this disclosure, are tested for their ability to reproducibly expel a 6 mm diameter cylindrical tablet. Applicators supplied with the commercial product VAGIFEM® estradiol (10 mcg) vaginal tablets, and having similar barrel and plunger rod dimensions, are also tested. In the tests, a unit is unwrapped and the presence of a tablet contained at the proximal end of the applicator is verified. The applicator is placed flat on a hard surface and gripped with the hand, such that a finger placed over the distal plunger end can depress the plunger. Pressure is gradually applied to the plunger end until the device is actuated and the tablet is expelled. The tablet distance from the applicator proximal tip is then measured. The table below shows results obtained from testing units from two manufacturing batches of the "test" applicators according to the present disclosure and four lot numbers of marketed VAGIFEM applicators. The VAGIFEM applicators appear to be constructed generally in accordance with the description in U.S. Pat. No. 5,860,946.

| | Distance Traveled (inches) | | | | | |
|---|---|---|---|---|---|---|
| | Test | | VAGIFEM ® | | | |
| Unit | K11K00542A | K11K00543A | AE70133 | AE70253 | AE70273 | AE70274 |
| 1 | 15 | 17 | 6 | 15 | 3 | 42 |
| 2 | 29 | 19 | 7 | 22 | 4 | 16 |
| 3 | 29 | 16 | 9 | 54 | 4 | 38 |

-continued

| | Distance Traveled (inches) | | | | | |
|---|---|---|---|---|---|---|
| | Test | | VAGIFEM ® | | | |
| Unit | K11K00542A | K11K00543A | AE70133 | AE70253 | AE70273 | AE70274 |
| 4 | 26 | 27 | 8 | 42 | 3 | 40 |
| 5 | 25 | 23 | 7 | 21 | 4 | 46 |
| 6 | 30 | 20 | 12 | 70 | 5 | 18 |
| 7 | 26 | 29 | 7 | 34 | 6 | 36 |
| 8 | 25 | 24 | 4 | 12 | 7 | 18 |
| 9 | 30 | 26 | 5 | 33 | 5 | 34 |
| 10 | 38 | 30 | 3 | 60 | 3 | 43 |
| 11 | 21 | 31 | 4 | 10 | 4 | 33 |
| 12 | 28 | 23 | 7 | 27 | 5 | 10 |
| Average | 26.83 | 23.75 | 6.58 | 33.33 | 4.42 | 31.17 |
| Std. Dev. | 5.54 | 5.03 | 2.47 | 19.57 | 1.24 | 12.29 |

Although the apparatus has been described herein with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope thereof. Thus, it is intended that the scope of the present disclosure includes all modifications and variations that are within the scope of the appended claims and their equivalents.

We claim:

1. An assembly for introducing a medicament into a body cavity, the assembly comprising:
    an elongate tube having a proximal end, a distal end, an outer surface, an inner surface and an opening extending from the distal end to the proximal end, the proximal end adapted to support a medicament, the elongate tube comprising at least one radial discontinuity adjacent the distal end and extending inwardly from the inner surface of the tube; and
    a plunger rod having an elongate body with a distal end and a proximal end, the proximal end of the elongate tube having a proximal cap, the plunger rod extending from the proximal end of the elongate tube to the distal end of the elongate tube and adapted to be slidably engaged within the tube.

2. The assembly of claim 1, wherein the plunger rod includes at least two axially spaced projections adjacent the distal end of the elongate body that cooperatively engages with longitudinally opposing surfaces of each of the at least one radial discontinuity, and wherein the at least one radial discontinuity on the elongate tube cooperatively engages between the at least two axially spaced projections on the elongate body of the plunger rod.

3. The assembly of claim 2, wherein when the at least one radial discontinuity on the elongate tube is cooperatively engaged between the at least two axially spaced projections on the elongate body of the plunger rod, spontaneous movement of the plunger rod distally or proximally with respect to the elongate tube is substantially prevented.

4. The assembly of claim 3, wherein the at least two axially spaced projections on the elongate body are positioned a sufficient distance from the distal end of the plunger rod such that when the at least one radial discontinuity on the elongate tube is cooperatively engaged between the at least two axially spaced projections, proximal movement of the plunger rod with respect to the elongate tube causes the proximal end of the plunger rod to expel a medicament from the proximal end of the elongate tube.

5. The assembly of claim 1, wherein the proximal end of the elongate tube contains a medicament.

6. The assembly of claim 5, wherein the medicament is a tablet.

7. The assembly of claim 6, wherein the tablet comprises an estrogen compound.

8. The assembly of claim 6, wherein the tablet comprises from about 10 mcg to about 25 mcg of an estrogen compound.

9. A method of depositing a medicament into a body cavity, the method comprising:
    inserting the distal end of the elongate tube of the assembly of claim 8 into the body cavity; and
    expelling the medicament into the body cavity.

10. The method of claim 9 wherein the step of expelling the medicament comprises applying proximally directed pressure to the proximal end of the plunger rod such that the plunger rod moves proximally with respect to the elongate tube causing the at least one radial discontinuity on the elongate tube to disengage from the at least two radial projections on the elongate body of the plunger rod.

11. The method of claim 10, wherein the medicament is a tablet.

12. The method of claim 11, wherein the tablet comprises an estrogen compound.

13. The method of claim 11, wherein the tablet comprises from about 10 mcg to about 25 mcg of the estrogen compound.

14. The assembly of claim 1, wherein the elongate body of the plunger rod comprises two intersecting beams extending from the distal end to the proximal end, such that elongate body has a cruciform-shaped cross section comprising four rays.

15. The assembly of claim 14, wherein two of the four rays each contain two axially spaced projections.

16. The assembly of claim 1, wherein the distal end of the plunger rod is undivided.

17. The assembly of claim 1, wherein the distal end of the plunger rod is blunt or rounded.

18. The assembly of claim 1, wherein the proximal end of the elongate tube further includes at least two tongues.

19. The assembly of claim 1, wherein the proximal cap is blunt.

20. The assembly of claim 1, wherein the proximal cap has a shape that complements a shape of the medicament.

21. The assembly of claim 1, wherein the proximal end of the elongate tube further comprises at least two lips adapted to prevent lateral movement of the medicament.

22. The assembly of claim 21, wherein the at least lips are biased inward from the outer surface of the elongate tube at its proximal end.

23. The assembly of claim 1, wherein the plunger rod further comprises a thumbpress on the distal end.

24. The assembly of claim 1, wherein the outer surface of the elongate tube comprises at least one roughened surface adapted to prevent slippage of the elongate tube between a user's fingers.

25. The assembly of claim 1, wherein each of the elongate tube and plunger rod are made from a material comprising one or more of polypropylene and high-density polyethylene.

26. An assembly for introducing a medicament into a body cavity, the assembly comprising:

an elongate tube having a proximal end, a distal end, an outer surface, an inner surface and an opening extending from the distal end to the proximal end, the proximal end having at least two tongues supporting a medicament, the elongate tube comprising at least one radial discontinuity adjacent the distal end and extending inwardly from the inner surface of the tube; and a plunger rod having an elongate body with a distal end and a proximal end, the plunger rod extending from the proximal end of the elongate tube to the distal end of the elongate tube and adapted to be slidably engaged within the tube, the plunger rod comprising at least two axially spaced projections adjacent the distal end of the elongate body, the at least one radial discontinuity on the elongate tube cooperatively engaged between the at least two axially spaced projections on the elongate body of the plunger rod such that spontaneous movement of the plunger rod distally or proximally with respect to the elongate tube is substantially prevented and the proximal end of the plunger rod is in position to expel the medicament into the body cavity upon forced proximal movement of the plunger rod.

* * * * *